(12) United States Patent
Liu et al.

(10) Patent No.: US 11,913,003 B2
(45) Date of Patent: Feb. 27, 2024

(54) METHOD FOR IMPROVING SOYBEAN TRANSFORMATION EFFICIENCY

(71) Applicant: BEIJING DABEINONG BIOTECHNOLOGY CO., LTD., Beijing (CN)

(72) Inventors: Yanhua Liu, Beijing (CN); Yuanyuan Wang, Beijing (CN); Zhiwei Jia, Beijing (CN); Qingfang Song, Beijing (CN)

(73) Assignee: BEIJING DABEINONG BIOTECHNOLOGY CO., LTD., Beijing (CN)

( * ) Notice: Subject to any disclaimer, the term of this patent is extended or adjusted under 35 U.S.C. 154(b) by 221 days.

(21) Appl. No.: 16/610,870

(22) PCT Filed: Apr. 13, 2018

(86) PCT No.: PCT/CN2018/082995
§ 371 (c)(1),
(2) Date: Nov. 4, 2019

(87) PCT Pub. No.: WO2018/205796
PCT Pub. Date: Nov. 15, 2018

(65) Prior Publication Data
US 2021/0277406 A1  Sep. 9, 2021

(30) Foreign Application Priority Data

May 9, 2017  (CN) .......................... 201710319417.8

(51) Int. Cl.
C12N 15/82 (2006.01)
(52) U.S. Cl.
CPC ....... C12N 15/821 (2013.01); C12N 15/8205 (2013.01); C12N 15/8278 (2013.01)
(58) Field of Classification Search
CPC ........................ C12N 15/8278; C12N 15/8274
See application file for complete search history.

(56) References Cited

U.S. PATENT DOCUMENTS

| 5,914,451 | A | * | 6/1999 | Martinell | ........... | C12N 15/8201 |
| | | | | | | 800/278 |
| 2006/0005276 | A1 | * | 1/2006 | Falco | ................. | C12N 15/8247 |
| | | | | | | 800/312 |
| 2014/0325700 | A1 | * | 10/2014 | Li | ..................... | C12N 15/8259 |
| | | | | | | 800/278 |
| 2015/0113681 | A1 | | 4/2015 | Zhong | | |
| 2017/0022515 | A1 | | 1/2017 | Wright et al. | | |
| 2019/0029257 | A1 | | 1/2019 | Xie et al. | | |
| 2019/0055576 | A1 | | 2/2019 | Xie et al. | | |
| 2019/0106705 | A1 | | 4/2019 | Xie et al. | | |

FOREIGN PATENT DOCUMENTS

| CN | 1984558 | A | | 6/2007 | | |
| CN | 103525864 | A | | 1/2014 | | |
| CN | 103740663 | A | | 4/2014 | | |
| CN | 105724140 | A | | 7/2016 | | |
| CN | 105724140 | A | * | 7/2016 | ............. | A01G 13/00 |
| CN | 105746255 | A | | 7/2016 | | |
| CN | 105766992 | A | | 7/2016 | | |
| CN | 105802933 | A | * | 7/2016 | ............. | A01N 25/32 |
| CN | 105802933 | A | | 7/2016 | | |
| CN | 106755061 | A | | 5/2017 | | |
| CN | 106755062 | A | | 5/2017 | | |
| CN | 107099548 | A | | 8/2017 | | |
| IN | 105724139 | A | | 7/2016 | | |

OTHER PUBLICATIONS

Hang et al.(SulE, a Sulfonylurea Herbicide De-Esterification Esterase from Hansschlegelia zhihuaiae S113. Applied and Environmental Microbiology 1962-1968, 2012) (Year: 2012).*
Padilla et al (Aminoglycoside antibiotics: structure, functions and effects on in vitro plant culture and genetic transformation protocols. Plant Cell Rep (2010) 29:1203-1213) (Year: 2010).*
Meristem Development: Ratchet Block, Nature Plant 2: p. 1, 2016 (Year: 2016).*
Aragão et al., Selection of transgenic meristematic cells utilizing a herbicidal molecule results in the recovery of fertile transgenic soybean [*Glycine max* (L.) Merril] plants at a high frequency. Theor Appl Genet. 101:1-6, 2000 (Year: 2000).*

(Continued)

*Primary Examiner* — Charles Logsdon
*Assistant Examiner* — Wayne Zhong
(74) *Attorney, Agent, or Firm* — James S. Keddie; Bozicevic, Field & Francis LLP

(57) ABSTRACT

The present invention relates to a method of improving soybean transformation efficiency, which comprises: transforming a plant cell using a recombinant vector containing a gene of interest and a gene encoding a sulfonylurea herbicide hydrolase; screening and culturing the transformed plant cell by external application of an ALS inhibitor, using the gene encoding the sulfonylurea herbicide hydrolase as a selective marker; selecting a plant cell that has not been killed and/or not been inhibited. The present invention firstly proposes that a selective agent is added to a proliferation medium and a differentiation medium in a manner of external application during plant transformation process, and optimizes the effective screening concentration range of the selective agent, so the transformation efficiency is remarkably increased, and the proportion of positive plants obtained in the progeny thereof is significantly increased; at the same time, the transgenic plants obtained by the transformation using the sulfonylurea herbicide hydrolase gene as a selective marker in the present invention have high commercial value, good resistance and genetic stability.

9 Claims, 3 Drawing Sheets
Specification includes a Sequence Listing.

(56) References Cited

OTHER PUBLICATIONS

Ray et al (Mutant acetolactate synthase gene is an efficient in vitro selectable marker for the genetic transformation of *Brassica juncea* (oilseed mustard). Journal of Plant Physiology 161, 1079-1083, 2004) (Year: 2004).*

What is plant transformation_ John Innes Centre_2017 (Year: 2017).*

Van der Vyver et al (In vitro selection of transgenic sugarcane callus utilizing a plant gene encoding a mutant form of acetolactate synthase. In Vitro Cell. Dev. Biol.—Plant 49:198-206, 2013) (Year: 2013).*

Ray et al (Mutant acetolactate synthase gene is an efficient et al selectable marker for the genetic transformation of *Brassica juncea* (oilseed mustard). Journal of Plant Physiology 161, 1079-1083, 2004) (Year: 2004).*

Yang et al (Target-site and non-target-site based resistance to the herbicide tribenuron-methyl in flixweed (*Descurainia sophia* L.) BMC Genomics 17:551, 2016) (Year: 2016).*

Trick et al., "Recent advances in soybean transformation", Plant Tissue Culture and Biotechnology, 1997, 3(1): 9-26.

Hang et al., "SulE, a Sulfonylurea Herbicide De-Esterification Esterase from Hansschlegelia zhihuaiae S113", Applied and Environmental Microbiology, Jan. 13, 2012, p. 1962-1968.

Zhang, "Construction of Sulfonylurea Herbicide Degrading Genetically Engineered Microorganism", Chinese Master's Theses Full-text Database, Thesis submitted to Nanjing Agricultural University, Jun. 2013.

Li et al., "Major selective reagents and resistance genes in plant genetic transformation", Cotton Molecular Breeding, China Agricultural University Press, May 2013, p. 182.

\* cited by examiner

METHOD FOR IMPROVING SOYBEAN TRANSFORMATION EFFICIENCY

CROSS-REFERENCE TO RELATED APPLICATIONS

This application is a § 371 national phase of International Application No. PCT/CN2018/082995, filed on Apr. 13, 2018, which claims benefit of Chinese Patent Application No. 201710319417.8, filed on May 9, 2017, which applications are incorporated by reference herein.

TECHNICAL FIELD

The present invention relates to a method of plant transformation, and particularly to a method for improving soybean transformation efficiency by external application of a selective agent.

BACKGROUND ART

With the rapid increase in types and areas of transgenic plants, the biosafety of selective marker genes in transgenic plants has become one of the most common concerns. Appropriate marker genes can provide a strong basis for obtaining true transformants and play a vital role in plant genetic transformation. Currently, marker genes widely used in plant genetic transformation include antibiotic resistance genes (such as NPTII gene, HPT gene, etc.) and herbicide resistance genes (such as PAT gene, EPSPS gene, bar gene, etc.). Since the selective marker genes are no longer useful once being successfully transformed, and even pose a potential threat to the ecological environment and food safety, the development of marker genes with biosafety is very important.

Acetolactate Synthase (hereinafter referred to as "ALS") is present in the growth process of plants. It can catalyze the pyruvate to acetolactate with high specificity and extremely high catalytic efficiency, resulting in the biosynthesis of branched-chain amino acids. Leucine, isoleucine and valine are three essential branched-chain amino acids in plants, and ALS is a key enzyme in the biosynthesis of leucine, valine and isoleucine, and its activity is also regulated by the feedback of the products valine and isoleucine.

ALS inhibitors are a group of known herbicides that inhibit the biosynthesis of valine, leucine and isoleucine in plants by inhibiting ALS activity in plants, leading to disruption of protein synthesis, thereby allowing the mitosis of plant cells stops at G1/S phase (DNA synthesis phase) and at G2/M phase, which interferes with the synthesis of DNA, and thus the cells cannot complete mitosis, resulting in chlorosis and yellowing of plant tissues, and plant growth is inhibited, eventually reaching the purpose of killing biological individuals. Therefore, ALS inhibitors are not only highly active, but also popular for their ultrahigh-efficiency, broad-spectrum, low-toxicity, low-residue, high-selectivity and good environmental compatibility, while the targets for inhibiting ALS inhibitors are not involved in humans and animals, so they are safe for humans and animals, and offer new options for marker genes and herbicide tolerance traits.

ALS inhibitors include sulfonylurea herbicides, imidazolinone herbicides, triazolopyrimidine herbicides, pyrimidinylthiobenzoic acid herbicides or sulfonylamino-carbonyl-triazolinone herbicides, etc. Although it has been reported that a sulfonylurea herbicide hydrolase gene can be used as a selective marker in plant transformation, the transformation efficiency thereof needs to be improved.

CONTENTS OF THE INVENTION

The object of the present invention is to provide a method for improving soybean transformation efficiency, which effectively overcomes the technical defects such as high false-positive proportion of plants and low transformation efficiency when ALS inhibitors are disposed in culture media in the prior art, and which provides a new option for large-scale genetic transformation and breeding of plants with herbicide tolerance traits.

To achieve the object, the present invention provides a method of selecting a transformed plant cell, comprising:
 transforming a plant cell using a recombinant vector containing a gene of interest and a gene encoding a sulfonylurea herbicide hydrolase;
 screening and culturing the transformed plant cell by external application of an ALS inhibitor, and using the gene encoding the sulfonylurea herbicide hydrolase as a selective marker; and
 selecting the plant cell that has not been killed and/or not been inhibited.

Further, the transformed plant cell is a plant cell transformed by an *Agrobacterium*-mediated process.

Further, the plant cell is a soybean cell.

Specifically, the external application includes dropping, spraying or smearing.

Specifically, the ALS inhibitor comprises a sulfonylurea compound, an imidazolinone compound, a triazolopyrimidine compound, a pyrimidinylthiobenzoic acid compound, or a sulfonylamino-carbonyl-triazolinone compound.

More specifically, the sulfonylurea compound is tribenuron methyl, sulfometuron methyl, pyrazosulfuron ethyl, halosulfuron methyl, thifensulfuron methyl, bensulfuron methyl, metsulfuron methyl, ethametsulfuron methyl or chlorimuron ethyl.

Alternatively, when the sulfonylurea compound is tribenuron methyl, 1-7 μg of tribenuron methyl is externally applied to per ml of a proliferation medium.

Preferably, when the sulfonylurea compound is tribenuron methyl, 3 μg of tribenuron methyl is externally applied to per ml of a proliferation medium.

Alternatively, the culturing is carried out in the proliferation medium for 5-9 days before tribenuron methyl is externally applied.

Preferably, the culturing is carried out in the proliferation medium for 7 days before tribenuron methyl is externally applied.

Based on the above technical solution, the sulfonylurea herbicide hydrolase comprises: (a) a protein composed of an amino acid sequence as shown in SEQ ID NO: 2; or (b) a protein derived from the protein in (a) by substitution and/or deletion and/or addition of one or several amino acids in the amino acid sequence as shown in SEQ ID NO: 2 and having an aryloxyalkanoate dioxygenase activity; or (c) a protein composed of an amino acid sequence having at least 90% sequence identity to SEQ ID NO: 2.

In order to achieve the above object, the present invention also provides a method for preparing a transgenic plant, the method is mediated by *Agrobacterium* and uses a gene encoding a sulfonylurea herbicide hydrolase as a selective marker, wherein, the method comprises:
 preparing an explant comprising at least a plant cell that can be transformed with an *Agrobacterium* strain;

contacting a region comprising at least the plant cell in the explant with an *Agrobacterium* strain comprising at least a gene encoding a sulfonylurea herbicide hydrolase;

screening and culturing the explant by external application of an ALS inhibitor;

selecting the transformed plant cell that has not been killed and/or not been inhibited; and regenerating the transformed plant cell to obtain a plant.

Further, the plant cell is a soybean cell.

Further, the explant is a cotyledon explant, a semi-seed explant or a semi-embryo seed explant.

Specifically, the external application includes dropping, spraying or smearing.

Specifically, the ALS inhibitor comprises a sulfonylurea compound, an imidazolinone compound, a triazolopyrimidine compound, a pyrimidinylthiobenzoic acid compound, or a sulfonylamino-carbonyl-triazolinone compound.

More specifically, the sulfonylurea compound is tribenuron methyl, sulfometuron methyl, pyrazosulfuron ethyl, halosulfuron methyl, thifensulfuron methyl, bensulfuron methyl, metsulfuron methyl, ethametsulfuron methyl or chlorimuron ethyl.

Alternatively, when the sulfonylurea compound is tribenuron methyl, 1-7 μg of tribenuron methyl is externally applied to per ml of a proliferation medium.

Preferably, when the sulfonylurea compound is tribenuron methyl, 3 μg of tribenuron methyl is externally applied to per ml of a proliferation medium.

Alternatively, the culturing is carried out in the proliferation medium for 5-9 days before tribenuron methyl is externally applied.

Preferably, the culturing is carried out in the proliferation medium for 7 days before tribenuron methyl is externally applied.

The regenerating the transformed plant cell to obtain a plant is specifically carried out by culturing and differentiating the transformed plant cell into a plant on a differentiation medium by external application of an ALS inhibitor.

Alternatively, when the ALS inhibitor is tribenuron methyl, 3-7 μg of tribenuron methyl is externally applied to per ml of the differentiation medium.

Preferably, when the ALS inhibitor is tribenuron methyl, 7 μg of tribenuron methyl is externally applied to per ml of the differentiation medium.

Alternatively, the culturing is carried out in the differentiation medium for 14-20 days before tribenuron methyl is externally applied.

Preferably, the culturing is carried out in the differentiation medium for 18 days before tribenuron methyl is externally applied.

Further, the *Agrobacterium* strain further comprises a gene conferring tolerance to an herbicide and/or a gene conferring resistance to an insect.

Specifically, the gene conferring tolerance to an herbicide encodes a herbicide-tolerant protein as follows: 5-enolpyruvylshikimate-3-phosphate synthase, glyphosate oxidoreductase, glyphosate-N-acetyltransferase, glyphosate decarboxylase, glufosinate acetyltransferase, α-ketoglutarate-dependent dioxygenase, dicamba monooxygenase, 4-hydroxyphenylpyruvate dioxygenase, acetolactate synthase, cytochrome protein and/or protoporphyrinogen oxidase.

Specifically, the gene conferring resistance to an insect comprises a Cry-like gene or a Vip-like gene.

Based on the above technical solution, the sulfonylurea herbicide hydrolase comprises: (a) a protein composed of an amino acid sequence as shown in SEQ ID NO: 2; or (b) a protein derived from the protein in (a) by substitution and/or deletion and/or addition of one or several amino acids in the amino acid sequence as shown in SEQ ID NO: 2 and having an aryloxyalkanoate dioxygenase activity; or (c) a protein composed of an amino acid sequence having at least 90% sequence identity to SEQ ID NO: 2.

In order to achieve the above object, the present invention also provides a method for transforming a soybean, which comprises:

removing one cotyledon and the first true leaf after the germination of a soybean seed, to obtain a naked meristem with one cotyledon;

performing pretreatment by inoculating the naked meristem with one cotyledon onto a pretreatment medium containing a cytokinin;

infesting the pretreated meristem block with an *Agrobacterium* strain comprising a gene encoding a sulfonylurea herbicide hydrolase;

screening and culturing the infested meristem block by external application of an ALS inhibitor, and using a gene encoding a sulfonylurea herbicide hydrolase as a selective marker;

selecting a plant cell that has not been killed and/or not been inhibited.

Specifically, the cytokinin is any one or any combination of 1 mg/L 6-benzylaminopurine and 2 mg/L zeatin.

Further, the pretreatment medium further comprises acetosyringone.

The pretreatment further comprises that the meristem block is subjected to ultrasonic treatment for 2-4 minutes after being wounded.

Specifically, the external application comprises dropping, spraying or smearing.

Specifically, the ALS inhibitor comprises a sulfonylurea compound, an imidazolinone compound, a triazolopyrimidine compound, a pyrimidinylthiobenzoic acid compound, or a sulfonylamino-carbonyl-triazolinone compound.

More specifically, the sulfonylurea compound is tribenuron methyl, sulfometuron methyl, pyrazosulfuron ethyl, halosulfuron methyl, thifensulfuron methyl, bensulfuron methyl, metsulfuron methyl, ethametsulfuron methyl or chlorimuron ethyl.

Alternatively, when the sulfonylurea compound is tribenuron methyl, 1-7 μg of tribenuron methyl is externally applied to per ml of a proliferation medium.

Preferably, when the sulfonylurea compound is tribenuron methyl, 3 μg of tribenuron methyl is externally applied to per ml of a proliferation medium.

Alternatively, the culturing is carried out in the proliferation medium for 5-9 days before tribenuron methyl is externally applied.

Preferably, the culturing is carried out in the proliferation medium for 7 days before tribenuron methyl is externally applied.

Further, the *Agrobacterium* strain further comprises a gene conferring tolerance to an herbicide and/or a gene conferring resistance to an insect.

Specifically, the gene conferring tolerance to an herbicide encodes a herbicide-tolerant protein as follows: 5-enolpyruvylshikimate-3-phosphate synthase, glyphosate oxidoreductase, glyphosate-N-acetyltransferase, glyphosate decarboxylase, glufosinate acetyltransferase, α-ketoglutarate-dependent dioxygenase, dicamba monooxygenase, 4-hydroxyphenylpyruvate dioxygenase, acetolactate synthase, cytochrome protein and/or protoporphyrinogen oxidase.

Specifically, the gene conferring resistance to an insect comprises a Cry-like gene or a Vip-like gene.

Based on the above technical solution, the sulfonylurea herbicide hydrolase comprises: (a) a protein composed of an amino acid sequence as shown in SEQ ID NO: 2; or (b) a protein derived from the protein in (a) by substitution and/or deletion and/or addition of one or several amino acids in the amino acid sequence as shown in SEQ ID NO: 2 and having an aryloxyalkanoate dioxygenase activity; or (c) a protein composed of an amino acid sequence having at least 90% sequence identity to SEQ ID NO: 2.

In order to achieve the above object, the present invention also provides a method for producing a stably transformed soybean plant, which comprises:

removing one cotyledon and the first true leaf after the germination of a soybean seed, to obtain a naked meristem with one cotyledon;

performing pretreatment by inoculating the naked meristem with one cotyledon onto a pretreatment medium containing a cytokinin;

infesting the pretreated meristem block with an *Agrobacterium* strain comprising a gene encoding a sulfonylurea herbicide hydrolase;

co-culturing the infested meristem block with the *Agrobacterium* strain;

screening and culturing the co-cultured meristem block by external application of an ALS inhibitor, and using a gene encoding a sulfonylurea herbicide hydrolase as a selective marker to select a transformed resistant tissue;

regenerating the transformed resistant tissue to obtain a soybean plant.

Specifically, the cytokinin is any one or any combination of 1 mg/L 6-benzylaminopurine and 2 mg/L zeatin.

Further, the pretreatment medium further comprises acetosyringone.

The pretreatment further comprises that the meristem block is subjected to ultrasonic treatment for 2-4 minutes after being wounded.

Specifically, the external application comprises dropping, spraying or smearing.

Specifically, the ALS inhibitor comprises a sulfonylurea compound, an imidazolinone compound, a triazolopyrimidine compound, a pyrimidinylthiobenzoic acid compound, or a sulfonylamino-carbonyl-triazolinone compound.

More specifically, the sulfonylurea compound is tribenuron methyl, sulfometuron methyl, pyrazosulfuron ethyl, halosulfuron methyl, thifensulfuron methyl, bensulfuron methyl, metsulfuron methyl, ethametsulfuron methyl or chlorimuron ethyl.

Alternatively, when the sulfonylurea compound is tribenuron methyl, 1-7 μg of tribenuron methyl is externally applied to per ml of a proliferation medium.

Preferably, when the sulfonylurea compound is tribenuron methyl, 3 μg of tribenuron methyl is externally applied to per ml of a proliferation medium.

Alternatively, the culturing is carried out in the proliferation medium for 5-9 days before tribenuron methyl is externally applied.

Preferably, the culturing is carried out in the proliferation medium for 7 days before tribenuron methyl is externally applied.

The regenerating the transformed resistant tissue to obtain a soybean plant is specifically carried out by culturing and differentiating the transformed resistant tissue into a soybean plant on a differentiation medium by external application of an ALS inhibitor.

Alternatively, when the ALS inhibitor is tribenuron methyl, 3-7 μg of tribenuron methyl is externally applied to per ml of the differentiation medium.

Preferably, when the ALS inhibitor is tribenuron methyl, 7 μg of tribenuron methyl is externally applied to per ml of the differentiation medium.

Alternatively, the culturing is carried out in the differentiation medium for 14-20 days before tribenuron methyl is externally applied.

Preferably, the culturing is carried out in the differentiation medium for 18 days before tribenuron methyl is externally applied.

Further, the *Agrobacterium* strain further comprises a gene conferring tolerance to an herbicide and/or a gene conferring resistance to an insect.

Specifically, the gene conferring tolerance to an herbicide encodes a herbicide-tolerant protein as follows: 5-enolpyruvylshikimate-3-phosphate synthase, glyphosate oxidoreductase, glyphosate-N-acetyltransferase, glyphosate decarboxylase, glufosinate acetyltransferase, α-ketoglutarate-dependent dioxygenase, dicamba monooxygenase, 4-hydroxyphenylpyruvate dioxygenase, acetolactate synthase, cytochrome protein and/or protoporphyrinogen oxidase.

Specifically, the gene conferring resistance to an insect comprises a Cry-like gene or a Vip-like gene.

Based on the above technical solution, the sulfonylurea herbicide hydrolase comprises: (a) a protein composed of an amino acid sequence as shown in SEQ ID NO: 2; or (b) a protein derived from the protein in (a) by substitution and/or deletion and/or addition of one or several amino acids in the amino acid sequence as shown in SEQ ID NO: 2 and having an aryloxyalkanoate dioxygenase activity; or (c) a protein composed of an amino acid sequence having at least 90% sequence identity to SEQ ID NO: 2.

The cloned genes, expression cassettes, vectors (e.g., plasmids), proteins and protein fragments, and transformed cells and plants of the present invention can be produced using standard methods.

The present invention can be used to express any gene of interest in a plant. The gene of interest may be a herbicide-tolerant gene, a disease-resistant gene or an insect-resistant gene, or a selection or evaluation marker, and contain a plant operable promoter, a coding region and a terminator region. The herbicide-tolerant gene comprises: AHAS gene tolerant to imidazolinone or sulfonylurea herbicides, pat or bar gene tolerant to glufosinate herbicides, EPSPS gene tolerant to glyphosate herbicides, AAD gene tolerant to 2,4-D herbicides, HPPD gene tolerant to HPPD inhibitors, and the like. The disease-resistant gene comprises antibiotic synthase genes, such as pyrrolnitrin synthase gene, plant-derived resistance genes, and the like. The insect-resistant gene comprises *Bacillus thuringiensis* insecticidal gene. The gene of interest may also encode an enzyme associated with a biochemical pathway, in which the expression of the enzyme may alter traits important for food, feed, nutraceutical and/or pharmaceutical production. The gene of interest can be located on a plasmid. The plasmid suitable for use in the present invention may contain one or more genes of interest and/or *Agrobacterium* may contain a different plasmid with a gene different from the genes of interest.

The plant in the present invention may be soybean, and the "soybean" refers to *Glycine max*. The method is based on that an *Agrobacterium*-mediated gene of interest is transferred into a soybean cell, followed by regeneration into a transformed soybean plant. The method of the invention is independent of a cultivar.

As used herein, the term "selective marker" refers to a gene or polynucleotide whose expression allows for the identification of a cell that has been transformed with a DNA construct or vector containing the gene or polynucleotide. The selective marker may provide resistance to a toxic compound, such as an antibiotic, a herbicide, and the like.

In the present invention, "acetolactate synthase" or "ALS" refers to an enzyme having an activity defined by the IUBMB enzyme nomenclature EC 2.2.1.6. The enzyme catalyzes the reaction between two pyruvate molecules to produce 2-acetolactate and $CO_2$. The enzyme requires thiamine diphosphate and may also be referred to as acetohydroxy acid synthase (AHAS).

In the present invention, "ALS inhibitor" refers to a compound which inhibits a wild-type ALS protein and is toxic to a cell containing a wild-type ALS. Such compounds include known herbicides, and mainly include sulfonylureas, imidazolinones, triazolopyrimidines, pyrimidinylthiobenzoic acids or sulfonylamino-carbonyl-triazolinones.

The sulfonylurea compounds which can be used in the present invention include: 1) phenylsulfonylureas, including chlorimuron ethyl, primisulfuron, 3-(4-ethyl-6-methoxy-1,3,5-triazin-2-yl)-1-(2,3-dihydro-1,1-dioxo-2-methylbenzo[b]thiophene-7-sulfonyl)-urea, 3-(4-ethoxy-6-ethyl-1,3,5-triazin-2-yl)-1-(2,3-dihydro-1,1-dioxo-2-methylbenzo[b]thiophene-7-sulfonyl)-urea, tribenuron methyl, metsulfuron methyl, chlorsulfuron, triasulfuron and sulfometuron methyl; 2) thienylsulfonylureas, such as thifensulfuron methyl; 3) pyrazolylsulfonylureas, including pyrazosulfuron ethyl and methyl 3-chloro-5-(4,6-dimethoxypyrimidin-2-yl-carbamoylsulfamonl)-1-methyl-pyrazole-4-carboxylate; 4) sulfone-hydrazine derivatives, including amidosulfuron and structural analogs thereof; 5) pyridylsulfonylureas, including nicosulfuron and DPX-E 9636; 6) phenoxysulfonylureas.

In the present invention, the genome of plant, plant tissue or plant cell refers to any genetic material in the plant, plant tissue or plant cell, which includes genomes of nucleus and plastid and mitochondrion thereof.

In the present invention, the "plant propagule" as used includes, but is not limited to, a plant sexual propagule and a plant asexual propagule. The plant sexual propagule includes, but is not limited to, a plant seed; the plant asexual propagule refers to a vegetative organ of a plant body or a special tissue which can produce a new plant under ex vivo conditions; the vegetative organ or specific tissue includes, but is not limited to, a root, a stem and a leave, for example: plants with roots as asexual propagules including strawberries and sweet potatoes; plants with stems as asexual propagules including sugar cane and potatoes (tubers), etc.; plants with leaves as asexual propagules including aloe vera and begonia.

In the present invention, the "resistance" is heritable and allows the growth and reproduction of a plant treated with a herbicide under a generally herbicidally effective condition. As recognized by those skilled in the art, a plant can be considered "resistant" even if the plant is significantly damaged by the herbicide treatment. In the present invention, the term "tolerance" is broader than the term "resistance", and includes "resistance" as well as the ability of a particular plant to increase the resistance to a herbicide-induced damage to various degrees, while the same herbicide dose generally results in a damage to the same genotype of wild-type plant.

In the present invention, the polynucleotides and/or nucleotides form a complete "gene" encoding a protein or polypeptide in a desired host cell. As readily recognized by those skilled in the art, the polynucleotides and/or nucleotides of the invention can be placed under the control of a regulatory sequence in a host of interest.

As well known to those skilled in the art, DNA typically exists in a double stranded form. In such arrangement, one chain is complementary to the other and vice versa. Since DNA is replicated and other complementary strands of DNA are produced in plants, the present invention encompasses the use of the polynucleotides exemplified in the Sequence Listing and their complementary strands. A "coding strand" as commonly used in the art refers to a strand that binds to an antisense strand. To express a protein in vivo, one strand of DNA is typically transcribed into a complementary strand of mRNA that is used as a template to translate the protein. mRNA is actually transcribed from the "antisense" strand of DNA. A "sense" or "encoding" strand has a series of codons (a codon is composed of three nucleotides, and a particular amino acid can be produced by reading the three at a time), which can be read as an open reading frame (ORF) to form a protein or peptide of interest. The invention also comprises a RNA that is functionally equivalent to the exemplified DNA.

The polynucleotide or nucleic acid molecule or fragment thereof of the present invention is hybridizable under stringent conditions with the sulfonylurea herbicide hydrolase gene of the present invention. Any conventional nucleic acid hybridization or amplification method can be used to identify the presence of the sulfonylurea herbicide hydrolase gene of the present invention. A nucleic acid molecule or a fragment thereof is capable of specifically hybridizing to another nucleic acid molecule under certain circumstances. In the present invention, if two nucleic acid molecules can form an anti-parallel double-stranded nucleic acid structure, it can be said that the two nucleic acid molecules are capable of specifically hybridizing each other. If two nucleic acid molecules exhibit complete complementarity, one of the nucleic acid molecules is said to be the "complement" of the other nucleic acid molecule. In the present invention, when each nucleotide of one nucleic acid molecule is complementary to a corresponding nucleotide of another nucleic acid molecule, the two nucleic acid molecules are said to exhibit "complete complementarity". Two nucleic acid molecules are said to be "minimally complementary" if they are capable of hybridizing to one another with sufficient stability such that they anneal under at least conventional "lowly stringent" conditions and bind to each other. Similarly, two nucleic acid molecules are said to be "complementary" if they are capable of hybridizing to one another with sufficient stability such that they anneal under conventional "highly stringent" conditions and bind to each other. Deviation from complete complementarity is permissible as long as such deviation does not completely prevent the two molecules from forming a double-stranded structure. In order for a nucleic acid molecule to function as a primer or probe, it is only necessary to ensure that it is sufficiently complementary in sequence to allow for the formation of a stable double-stranded structure under the used particular solvent and salt concentration.

In the present invention, a substantially homologous sequence is a nucleic acid molecule that is capable of specifically hybridizing to a complementary strand of another matched nucleic acid molecule under highly stringent conditions. Suitable stringent conditions for promoting DNA hybridization comprise, for example, treatment with 6.0× sodium chloride/sodium citrate (SSC) at about 45° C., followed by washing with 2.0×SSC at 50° C., and these conditions are known to those skilled in the art. For example, the salt concentration in the washing step can be selected from lowly stringent conditions of about 2.0×SSC and 50° C. to highly stringent conditions of about 0.2×SSC and 50° C. Further, the temperature conditions in the washing step can be raised from lowly stringent conditions of room temperature such as about 22° C. to highly stringent conditions of about 65° C. Both the temperature conditions and the salt concentration can be changed, or one of them remains unchanged while the other variable changes. Preferably, the stringent conditions of the present invention may comprise: specifically hybridizing with the nucleotide sequence of the sulfonylurea herbicide hydrolase of the present invention at 65° C. in a 6×SSC, 0.5% SDS solution, and then washing the membrane once with each of 2×SSC, 0.1% SDS, and 1×SSC, 0.1% SDS.

Therefore, a sequence having herbicide tolerance activity and hybridizing under stringent conditions to the nucleotide sequence of the sulfonylurea herbicide hydrolase of the present invention is included in the present invention. These sequences are at least about 40%-50%, about 60%, 65% or 70%, even at least about 75%, 80%, 85%, 90%, 91%, 92%, 93%, 94%, 95%, 96%, 97%, 98%, 99% or greater homologous to the sequences of the invention.

The invention provides functional proteins. In the present invention, "functional activity" (or "activity") refers to that the protein/enzyme usable in the invention (alone or in combination with other proteins) has the ability to degrade an herbicide. The plant producing the protein of the invention preferably produces an "effective amount" of the protein such that when the plant is treated with the herbicide (at a general dosage level, unless otherwise stated), the level of protein expression is sufficient to give the plant complete or partial resistance or tolerance to the herbicide. The herbicide can be used in an amount which normally kills the target plant, normal field amount and concentration. Preferably, the transformed plants and plant cells of the invention have resistance or tolerance to sulfonylurea herbicides, i.e., the transformed plants and plant cells can be grown in the presence of an effective amount of a sulfonylurea herbicide, for example, when the sulfonylurea herbicide is tribenuron methyl, the effective amount is 0.5-15 mg/L.

In the present invention, the genes and proteins include not only specific exemplary sequences, but also portions and/or fragments (including those within and/or having terminal deletion in comparison with the full length proteins), variants, mutants, substitution products (proteins with alternative amino acids), chimeras and fusion proteins, which retain the herbicide tolerance activity characteristics of the specific exemplary proteins. The "variant" or "variation" refers to a biologically active protein having the same or substantially the same herbicide tolerance as the protein of interest.

In the present invention, "fragment" or "truncation product" of a DNA molecule or protein sequence refers to that a portion of the original DNA or protein sequence (nucleotide or amino acid) as involved or an artificially engineered form thereof (e.g., a sequence suitable for plant expression) has a change in length in comparison with the foregoing sequence, but is of sufficient length to ensure that the (encoded) protein is a herbicide-tolerant protein.

Due to the abundance of the genetic codes, a variety of different DNA sequences may encode the same amino acid sequence. Those skilled in the art can produce these alternative DNA sequences that encode identical or substantially identical proteins. These different DNA sequences fall within the scope of the invention. The "substantially identical" sequence refers to a sequence that has an amino acid substitution, deletion, addition or insertion but does not substantially affect herbicide tolerance activity, which also comprises fragments thereof that retain the herbicide tolerance activity.

In the present invention, the substitution, deletion or addition of an amino acid sequence is a conventional technique in the art, and it is preferred that such an amino acid change is: a small change in properties, that is, a conservative amino acid substitution that does not significantly affect the folding and/or activity of the protein; a small deletion, typically a deletion of about 1-30 amino acids; a small amino- or carboxy-terminal extension, such as an amino-terminal extension of one methionine residue; and a small linker peptide, for example about 20-25 residues in length.

Examples of conservative substitutions are substitutions occurring within the following groups of amino acid: alkaline amino acids (such as arginine, lysine, and histidine), acidic amino acids (such as glutamic acid and aspartic acid), polar amino acids (such as glutamine, asparagine), hydrophobic amino acids (such as leucine, isoleucine and valine), aromatic amino acids (such as phenylalanine, tryptophan and tyrosine), and small molecules amino acids (such as glycine, alanine, serine, threonine, and methionine). Those amino acid substitutions that generally do not alter a particular activity are well known in the art and have been described, for example, by N. Neurath and R. L. Hill, "Protein", published in 1979 at New York Academic Press. The most common interchanges are: Ala/Ser, Val/Ile, Asp/Glu, Thu/Ser, Ala/Thr, Ser/Asn, Ala/Val, Ser/Gly, Tyr/Phe, Ala/Pro, Lys/Arg, Asp/Asn, Leu/Ile, Leu/Val, Ala/Glu and Asp/Gly, and their opposite interchanges.

It will be apparent to those skilled in the art that such substitutions can occur outside of the regions that are important for molecular function and still produce active polypeptides. For the polypeptides of the invention, amino acid residues necessary for their activity and thus selected for unsubstituted, can be identified according to methods known in the art, such as site-directed mutagenesis or alanine scanning mutagenesis (see, for example, Cunningham and Wells, 1989, Science 244: 1081-1085). The latter technique introduces a mutation at each positively charged residue in the molecule, and detects the herbicide resistance activity of the resulting mutant molecule, thereby determining an amino acid residue important for the activity of the molecule. The substrate-enzyme interaction site can also be determined by analysis of its three-dimensional structure, which can be determined by techniques such as nuclear magnetic resonance analysis, crystallography or photoaffinity labeling (see, for example, de Vos et al., 1992, Science 255: 306-312; Smith et al, 1992, J. Mol. Biol 224: 899-904; Wlodaver et al, 1992, FEBS Letters 309: 59-64).

In the present invention, the amino acid sequence encoding a sulfonylurea herbicide hydrolase includes, but is not limited to, the sequence involved in the sequence listing of the present invention, and an amino acid sequence having a certain homology thereto is also included in the present invention. The sequence similarity/identity of these sequences to the sequences of the invention is typically greater than 60%, preferably greater than 75%, more preferably greater than 80%, even more preferably greater than 90%, and may be greater than 95%. Preferred polynucleotides and proteins of the invention may also be defined according to a more specific range of identity and/or similarity. For example, in comparison with the exemplary sequence of the present invention, these sequences have 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity and/or similarity.

The regulatory sequences of the present invention include, but are not limited to, a promoter, a transit peptide, a terminator, an enhancer, a leader sequence, an intron, and other regulatory sequences operably linked to the sulfonylurea herbicide hydrolase gene.

The promoter is a promoter expressible in a plant, and the "promoter expressible in a plant" refers to a promoter which ensures expression of a coding sequence linked thereto in a plant cell. The promoter expressible in a plant can be a constitutive promoter. Examples of promoters that direct constitutive expression in plants include, but are not limited to, 35S promoter derived from cauliflower mosaic virus, maize Ubi promoter, promoter of rice GOS2 gene, and the like. Alternatively, the promoter expressible in a plant may be a tissue-specific promoter, such as PEP carboxylase promoter, that is, the level of coding sequence expression directed by the promoter in some tissues of the plant, such as in green tissue, is higher than that in other tissues of the plant (which can be determined by a conventional RNA assay). Alternatively, the promoter expressible in a plant can be a wound-inducible promoter. The wound-inducible promoter or a promoter that directs a wound-inducible expression pattern refers to that when a plant is subjected to mechanical or insect-grazing wounding, the expression of coding sequence under control of the promoter is significantly improved compared to normal growth conditions. Examples of wound-inducible promoter include, but are not limited to, promoters of potato and tomato protease inhibitory genes (pinI and pinII), and maize protease inhibitory gene (MPI).

The transit peptide (also known as secretion signal sequence or targeting sequence) directs a transgenic product to a specific organelle or cell compartment, and for a receptor protein, the transit peptide can be heterologous, for example, targeting chloroplast by using a sequence coding chloroplast transit peptide, or targeting endoplasmic reticulum by using a 'KDEL' retaining sequence, or targeting CTPP-targeted vacuole by using a barley plant lectin gene.

The leader sequence includes, but is not limited to, a picornavirus leader sequence, such as an EMCV leader sequence (5' non-coding region of encephalomyocarditis virus); a potato Y potyvirus leader sequence, such as a MDMV (maize dwarf mosaic virus) leader sequence; an human immunoglobulin protein heavy chain binding protein (BiP); an untranslated leader sequence of capsid protein mRNA of alfalfa mosaic virus (AMV RNA4); a tobacco mosaic virus (TMV) leader sequence.

The enhancer includes, but is not limited to, a cauliflower mosaic virus (CaMV) enhancer, a figwort mosaic virus (FMV) enhancer, a carnation etched ring virus (CERV) enhancer, and a cassava vein mosaic virus (CsVMV) enhancer, a mirabilis mosaic virus (MMV) enhancer, a cestrum yellow leaf curl virus (CmYLCV) enhancer, a cotton leaf curl Multan virus (CLCuMV) enhancer, a commelina yellow mottle virus (CoYMV) enhancer, and peanut chlorotic streak virus (PCLSV) enhancer.

For the application in monocotyledons, the intron includes, but is not limited to, maize hsp70 intron, maize ubiquitin intron, Adh intron 1, sucrose synthase intron, or rice Act1 intron.

For the application in dicotyledons, the intron includes, but is not limited to, CAT-1 intron, pKANNIBAL intron, PIV2 intron, and "super ubiquitin" intron.

The terminator may be a suitable polyadenylation signal sequence that functions in plants, including but not limited to, a polyadenylation signal sequence derived from *Agrobacterium tumefaciens* nopaline synthase (NOS) gene, a polyadenylation signal sequence derived from protease inhibitor II (pinII) gene, a polyadenylation signal sequence derived from pea ssRUBISCO E9 gene, and a polyadenylation signal sequence derived from α-tubulin gene.

In the present invention, "effective linked" refers to a linkage of nucleic acid sequences said linkage allows one sequence to provide the function required for the linked sequence. The "effective linked" in the present invention may be such that a promoter is linked to a sequence of interest so that the transcription of the sequence of interest is controlled and regulated by the promoter. When the sequence of interest encodes a protein and the expression of the protein is desired, the "effective linked" means that the promoter is linked to the sequence in a manner such that the resulting transcript is efficiently translated. If the linkage of the promoter to the coding sequence is a transcript fusion and it is desired to effect the expression of the encoded protein, such linkage is made so that the first translation initiation codon in the resulting transcript is the initiation codon of the coding sequence. Alternatively, if the linkage of the promoter to the coding sequence is a translation fusion and it is desired to effect the expression of the encoded protein, such linkage is made so that the first translation initiation codon contained in the 5' untranslated sequence is linked to the promoter, and the linkage manner results in that the resulting translation product is in frame with the translational open reading frame encoding the desired protein. Nucleic acid sequences that may be "effective linked" include, but are not limited to, sequences that provide gene expression function (i.e., gene expression elements, such as promoters, 5' untranslated regions, introns, protein coding regions, 3' untranslated regions, polyadenylation sites and/or transcription terminators), sequences that provide DNA transfer and/or integration functions (i.e., T-DNA border sequences, site-specific recombinase recognition sites, integrase recognition sites), sequences that provide selective functions (i.e., antibiotic resistance markers, biosynthetic genes), sequences that provide function of scoring markers, sequences that facilitate sequence manipulation in vitro or in vivo (i.e., polylinker sequences, site-specific recombination sequences), and sequences that provide replication function (i.e., bacterial replication origin sequences, autonomously replicating sequences, centromeric sequences).

In the present invention, the term "host cell" refers to a cell containing a recombinant nucleic acid of interest in a host cell genome or an extrachromosomal vector autonomously replicating independently from the genome of the host cell. The host cell can be of any cell type.

In the present invention, the term "transformation" refers to that a DNA is introduced into a cell such that the DNA is maintained in the cell as an extrachromosomal element or a chromosomal integrant.

The polynucleotide may be integrated into a genome of a host cell or present on a vector that replicates autonomously in the host cell.

In the present invention, when an exogenous DNA is introduced into a plant, for example, a gene or an expression cassette or a recombinant vector, which encodes the sulfonylurea herbicide hydrolase, is introduced into a plant cell, the conventional transformation methods include, but are not limited to, *Agrobacterium*-mediated transformation, micro-emission bombardment, direct ingestion of DNA into protoplasts, electroporation, or whisker silicon-mediated DNA introduction.

In the present invention, different *Agrobacterium* strains can be used, which include, but are not limited to, *Agrobacterium tumefaciens* and *Agrobacterium rhizogenes*. Preferably, a transformable strain is used. Suitable *Agrobacterium tumefaciens* strains include strain A208, strain EHA101, and strain LBA4404. Suitable *Agrobacterium rhizogenes* strain includes strain K599. The construction of transformable *Agrobacterium* vectors is well known in the art.

The transformed plant cells are cultured in the presence of a selective agent. Preferably, the transformation is carried out using sulfonylurea herbicide hydrolase (SULE) gene, and the transformed gene is cultured in the presence of a sulfonylurea herbicide. The SULE gene-transformed plant cells are selectively grown in a medium containing a sulfonylurea herbicide as a selective agent.

The present invention involves in a transgenic plant containing a heterologous nucleic acid (i.e., a cell or tissue transformed according to the method of the present invention), as well as a seed and a progeny produced by the transgenic plant. Methods for culturing the transformed cell into a useful cultivar are well known to those skilled in the art. Plant tissue in vitro culture techniques and whole plant regeneration techniques are also well known. Correspondingly, the "seed" includes seeds of these transformed plants as well as seeds produced by the transformed plant progenies. The "plant" includes not only transformed and regenerated plants, but also progenies of the transformed and regenerated plants produced by the methods of the present invention.

Successfully transformed plants can be screened from the plants produced by the methods of the present invention. To develop improved plants and seed lines, the seeds and progeny plants of the regenerated plants of the present invention can be continuously screened and selected to persist the transgenic and integrated nucleic acid sequences. Thus, the desired transgenic nucleic acid sequence can be introduced (i.e., introgressed or mated) into other genetic lines, such as certain original varieties or commercially useful lines or varieties. Methods for introgression of a gene of interest into a genetic plant line can be accomplished by a variety of techniques well known in the art, including methods of conventional breeding, protoplast fusion, cell nuclear transfer, and chromosome transfer. Breeding methods and techniques are also well known in the art. The transgenic plants and inbred lines obtained according to the present invention can be used to produce commercially valuable hybrid plants and crops.

The present invention provides a method for improving soybean transformation efficiency, which has the following advantages:

1. Unlike the prior art, in which the selective agent is disposed in a culture medium, the present invention first proposes that a selective agent (such as tribenuron methyl) is externally applied (especially, added dropwise) to a proliferation medium and a differentiation medium during the plant transformation process, and the positive plant rate and transformation efficiency of the progeny are significantly improved, which provides a new idea for the use of selective agent in the plant transformation process.
2. The screening system is optimized. The present invention adopts the *Agrobacterium*-mediated transformation method, which not only provides a new usage mode and screening method for sulfonylurea herbicide as a selective agent, but also optimizes the effective screening concentration range, thereby obtaining transgenic plants with resistance to ALS inhibitor.
3. High transformation efficiency and reduced transformation costs. When a sulfonylurea herbicide is used as a selective agent in the present invention, the screening is carried out by adding a selective agent with an optimized screening concentration via external application (especially dropping), and the proportion of positive plants in the progeny is significantly increased, and the transformation efficiency can be improved by up to 20% or more, while the external application (especially dropping) can make effective use of the selective agent and reduce the cost of plant genetic transformation.
4. High commercial value. Sulfonylurea herbicide is a systematic herbicide, and the transgenic plant obtained by the present invention has high tolerance to the sulfonylurea herbicide, and the progeny thereof can be stably inherited, and can be directly developed into a sulfonylurea-tolerant crop useful in product development.

The technical solution of the present invention will be further described in detail below through the accompanying drawings and examples.

SPECIFIC MODELS FOR CARRYING OUT THE INVENTION

The technical solution of the method for improving soybean transformation efficiency of the present invention is further illustrated by specific examples below.

Figure 1:
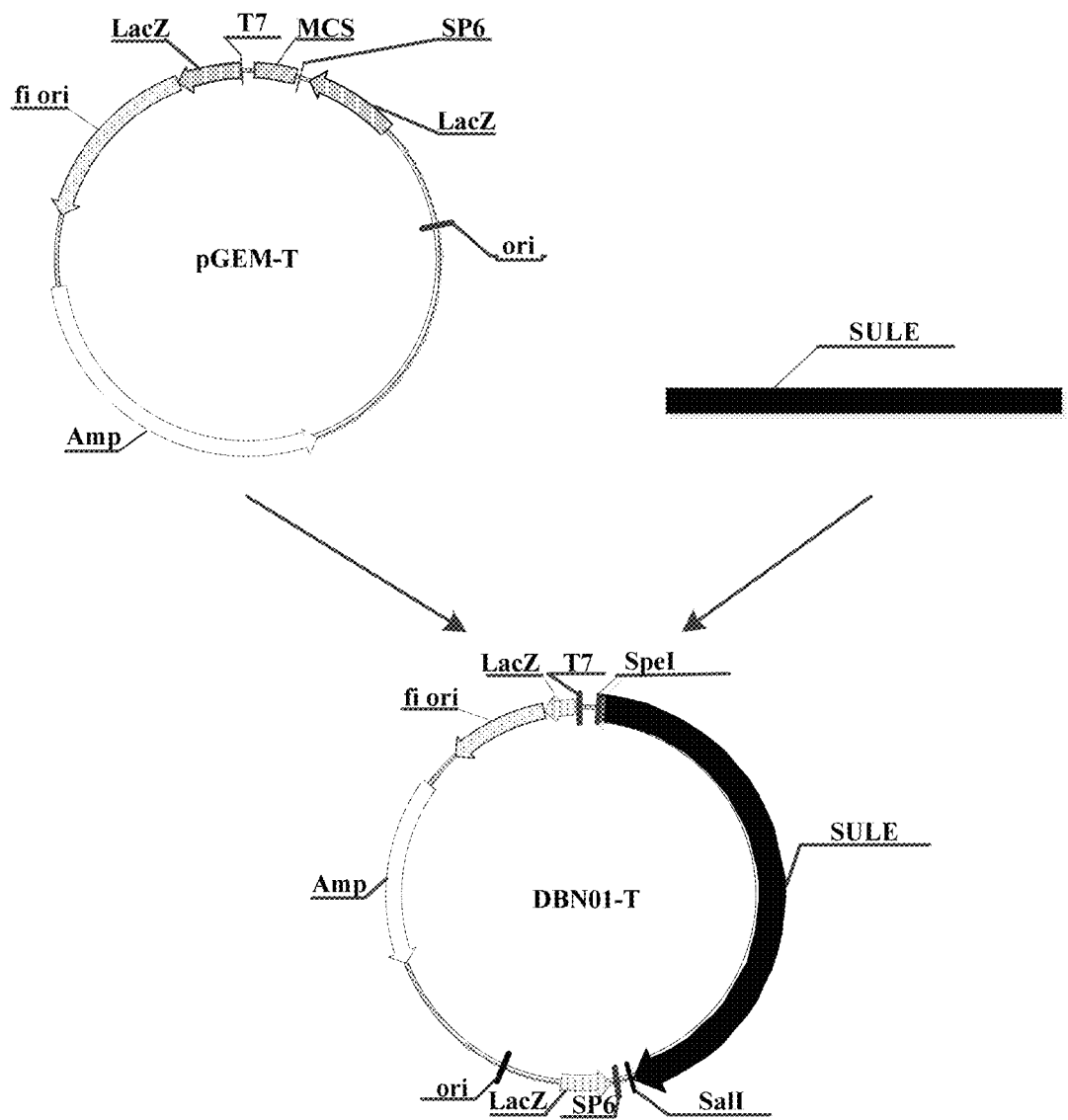
FIG. 1 shows a flow diagram for construction of a recombinant cloning vector DBN01-T useful in the method for improving soybean transformation efficiency of the present invention.

Example 1: Construction of Recombinant Expression Vector and Transformation of *Agrobacterium* with Recombinant Expression Vector 1. Construction of Recombinant Cloning Vector Containing Gene of Interest SULE nucleotide sequence was ligated into a cloning vector pGEM-T (Promega, Madison, USA, CAT: A3600), and the procedure was carried out according to the specification of pGEM-T vector product of Promega Company to obtain a recombinant cloning vector DBN01-T, and the construction process thereof was as shown in FIG. 1 (wherein Amp represented ampicillin resistance gene; f1 represented the replication origin of phage f1; LacZ was LacZ initiation codon; SP6 was SP6 RNA polymerase promoter; T7 was T7 RNA polymerase promoter; SULE was sulfonylurea herbicide hydrolase gene nucleotide sequence (SEQ ID NO: 1); MCS was multiple cloning site).

The recombinant cloning vector DBN01-T was then transformed into *E. coli* T1 competent cells (Transgen, Beijing, China, CAT: CD501) by heat shock method under heat shock conditions: 50 μl of *E. coli* T1 competent cells, 10 μl of plasmid DNA (recombinant cloning vector DBN01-T), subjected to water bath at 42° C. for 30 seconds; subjected to shaking culture at 37° C. for 1 hour (shaken at 100 rpm using a shaking table), and cultured for growing overnight on a LB plate (tryptone 10 g/L, yeast extract 5 g/L, NaCl 10 g/L, agar 15 g/L, adjusted to pH 7.5 with NaOH) of ampicillin (100 mg/L) that was surface-coated with IPTG (isopropylthio-β-D-galactoside) and X-gal (5-bromo-4-chloro-3-indolyl-β-D-galactoside). White colonies were picked and cultured overnight in a LB liquid medium (tryptone 10 g/L, yeast extract 5 g/L, NaCl 10 g/L, ampicillin 100 mg/L, adjusted to pH 7.5 with NaOH) at 37° C. The plasmid was extracted by alkaline method: the bacterial solution was centrifuged at 12000 rpm for 1 mM, the supernatant was removed, the precipitated bacterial cells were suspended in 100 μl of ice-precooled solution I (25 mM Tris-HCl, 10 mM EDTA (ethylenediamine tetraacetic acid), 50 mM glucose, pH 8.0); 200 μl of freshly prepared solution II (0.2 M NaOH, 1% SDS (sodium dodecyl sulfate)) was added to the tube, the tube was inverted for 4 times for mixing, placed on ice for 3-5 min; 150 μl of ice-cooled solution III (3 M potassium acetate, 5 M acetic acid) was added and mixed well immediately, placed on ice for 5-10 mM; centrifuged at 4° C. and 12000 rpm for 5 min, the supernatant was added with 2 times volume of absolute ethanol, mixed and stood for 5 mM at room temperature; centrifuged at 4° C. and 12000 rpm for 5 min, the supernatant was discarded, the precipitate was washed with 70% (V/V) ethanol and air-dried; 30 μl of TE (10 mM Tris-HCl, 1 mM EDTA, pH 8.0) containing RNase (20 μg/ml) was added to dissolve the precipitate; water-bath at 37° C. was performed for 30 mM to digest RNA; and the product was stored at −20° C. for later use.

After the extracted plasmid was identified by ApaI and EcoRV digestion, the positive clone was verified by sequencing. The result showed that the SULE gene sequence inserted into the recombinant cloning vector DBN01-T was the nucleotide sequence shown in SEQ ID NO: 1 in the Sequence Listing.

2. Construction of Recombinant Expression Vector Containing Gene of Interest

Figure 2:
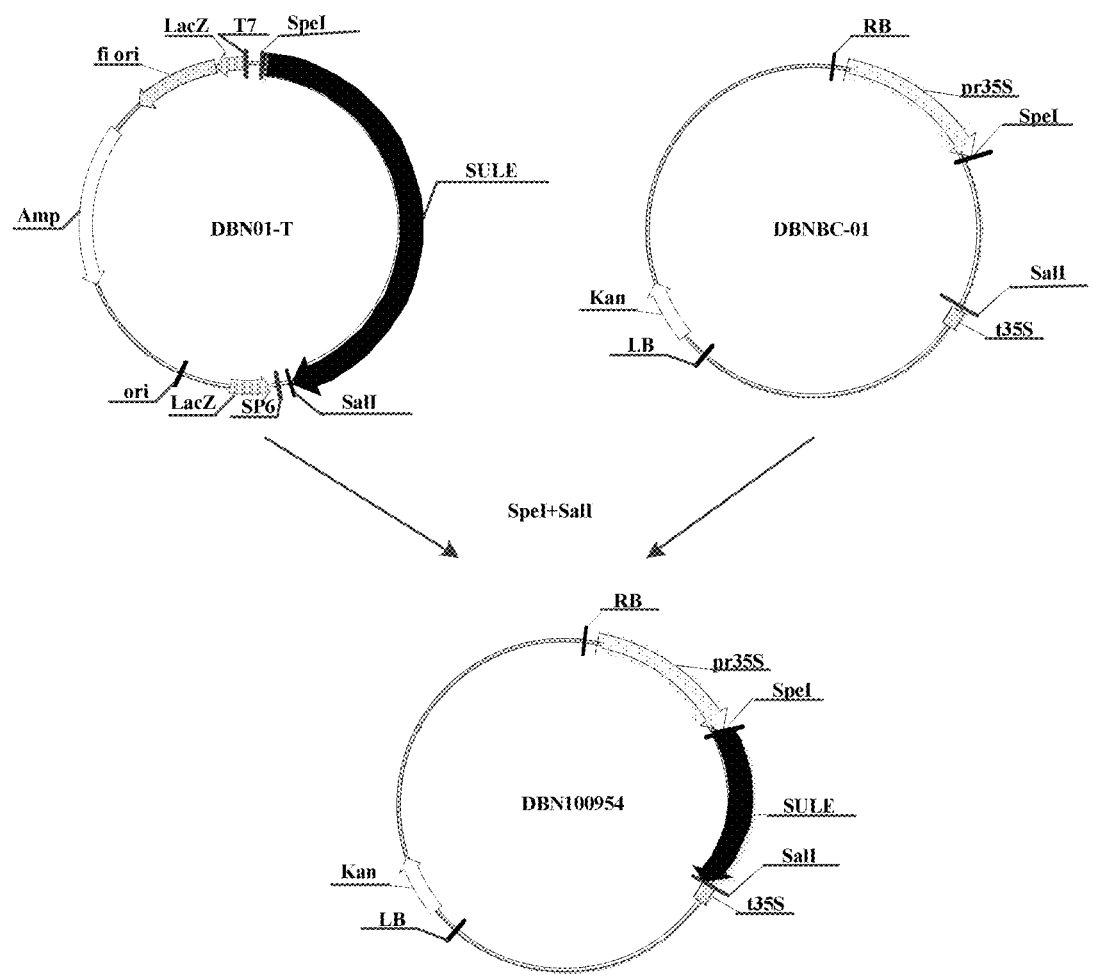
FIG. 2 shows a flow diagram for construction of a recombinant cloning vector DBN100954 useful in the method for improving soybean transformation efficiency of the present invention.

The recombinant cloning vector DBN01-T and the expression vector DBNBC-01 (vector framework: pCAMBIA2301 (provided by CAMBIA)) were digested with restriction endonucleases SpeI and SalI, respectively, and the excised SULE gene sequence was inserted between the SpeI and SalI sites of the expression vector DBNBC-01; the construction of vector by conventional enzyme digestion method was well known to those skilled in the art, and the recombinant expression vector DBN100954 was constructed and the construction process thereof was shown in FIG. 2 (Kan: kanamycin gene; RB: right border; pr35S: promoter of cauliflower mosaic virus 35S gene (SEQ ID NO: 3); SULE: sulfonylurea herbicide hydrolase gene nucleotide sequence (SEQ ID NO: 1, the amino acid sequence thereof was shown in SEQ ID NO: 2); t35S: terminator of cauliflower mosaic virus 35S gene (SEQ ID NO: 4); LB: left border).

The recombinant expression vector DBN100954 was transformed into *E. coli* T1 competent cells by heat shock method, and the heat shock conditions were: 50 μl of *E. coli* T1 competent cells, 10 μl of plasmid DNA (recombinant expression vector DBN100954), subjected to water bath at 42° C. for 30 seconds; subjected to shaking culture at 37° C. for 1 hour (shaken at 200 rpm using a shaking table); then cultured at 37° C. for 12 hours on a LB solid plate containing 50 mg/L kanamycin (trypeptin 10 g/L, yeast extract 5 g/L, NaCl 10 g/L, agar 15 g/L, adjusted to pH 7.5 with NaOH), white colonies were picked and cultured at 37° C. overnight in a LB liquid medium (trypeptin 10 g/L, yeast extract 5 g/L, NaCl 10 g/L, kanamycin 50 mg/L, adjusted to pH 7.5 with NaOH). The plasmid was extracted by alkaline method. The extracted plasmid was identified by restriction endonucleases SpeI and Sal I digestion, and the positive clones were identified by sequencing. The results showed that the nucleotide sequence between the SpeI and SalI sites of the recombinant expression vector DBN100954 was the nucleotide sequence shown in SEQ ID NO: 1 in the Sequence Listing, that was, the SULE nucleotide sequence.

3. Transformation of *Agrobacterium* with Recombinant Expression Vector

The correctly constructed recombinant expression vector DBN100954 was transformed into *Agrobacterium* LBA4404 (Invitrogen, Chicago, USA, CAT: 18313-015) by liquid nitrogen method, and the transformation conditions were: 100 μL of *Agrobacterium* LBA4404, 3 μL of plasmid DNA (recombinant expression vector); placed in liquid nitrogen for 10 minutes, subjected to 37° C. water bath for 10 minutes; the transformed *Agrobacterium* LBA4404 was inoculated in a LB tube and cultured at a temperature of 28° C. and 200 rpm for 2 hours, coated on a LB plate containing 50 mg/L rifampicin and 100 mg/L kanamycin until a positive monoclone grew, the monoclone was picked and cultured, and the plasmid thereof was extracted and verified by enzyme digestion using restriction endonuclease ApaLI and EcoRV, and the results showed that the recombinant expression vector DBN100954 was completely correct.

Example 2: Acquisition of Transgenic Soybean Plant

Disinfection of soybean seeds: Fully dried mature soybean seeds (Zhonghuang 13) were taken and placed in a culture dish, and the amount thereof was about ⅓ of the volume of the dish. The dish was placed in a desiccator in a fume hood, a 250 ml large beaker containing 120 ml of sodium hypochlorite was placed in the desiccator. 6 ml of concentrated hydrochloric acid was added dropwise along the beaker wall, then the desiccator was closed and sealed with lid, and the glass of the fume hood was closed at the same time, so that the soybean seeds were exposed to the chlorine gas in the fume hood for 3 hours for sterilization. After the lid of dish was covered, the dish was took out and shaken for 2-3 minutes. The above procedure was repeated once, and the culture dish containing the soybean seeds was placed in the fume hood for overnight sterilization.

Germination of soybean seed: 15 sterilized soybean seeds were inoculated on a soybean germination medium (B5 salt 3.1 g/L, B5 vitamin, sucrose 20 g/L, agar 8 g/L, pH 5.6) for germination, in which the culture conditions were as follows: temperature 25±1° C., photoperiod was 16/8 h, and the umbilical sides of the soybean seeds were inserted in the medium, and the culture dish was wrapped with plastic wrap after inoculation.

In the germination medium of the present example, the B5 salt might also be N6 salt (concentration was 3.95 g/L) or MS salt (concentration was 4.3 g/L), and the sucrose concentration might be 5-100 g/L; the above components might be arbitrarily combined in ranges of their concentrations, but the germination medium (B5 salt 3.1 g/L, B5 vitamin, sucrose 20 g/L, agar 8 g/L, pH 5.6) was preferred.

Pretreatment of explant: After 1 day of germination, one cotyledon and the first true leaf were removed, and the naked meristem was inoculated into a pretreatment medium containing cytokinin (MS salt 4.3 g/L, B5 vitamin, sucrose 20 g/L, agar 8 g/L, 2-morpholine ethanesulfonic acid (MES) 4 g/L, zeatin (ZT) 2 mg/L, 6-benzylaminopurine (6-BAP) 1 mg/L, acetosyringone (AS) 40 mg/L, pH 5.3), wherein cytokinin was added in this step to make the cells in the meristem zone active, and AS was also added to the medium to promote the integration of exogenous gene, the pretreatment was carried out for 2-5 days, preferably 3 days, and the pre-treated meristem block was subjected to wound with a scalpel blade (cut at least 3 times, preferably 5 times), and ultrasonic treatment was performed for 2-5 minutes, preferably 3 minutes after the wound.

In the pretreatment medium of the present example, the MS salt might also be N6 salt (concentration was 3.95 g/L) or B5 salt (concentration was 3.1 g/L), and the concentration of sucrose might be 5-100 g/L, the concentration of MES might be 0.1-5 g/L, the concentration of ZT might be 0.1-5 mg/L, the concentration of 6-BAP might be 0.1-5 g/L, and the concentration of AS might be 10-50 mg/L; the above components might be arbitrarily combined in their concentration ranges, but the pretreatment medium (MS salt 4.3 g/L, B5 vitamin, sucrose 20 g/L, agar 8 g/L, MES 4 g/L, ZT 2 mg/L, 6-BAP 1 mg/L, AS 40 mg/L, pH 5.3) was preferred.

Preparation of Agrobacterium liquid: Agrobacterium strain was taken out from −80° C. refrigerator, and the Agrobacterium single colony containing DBN100954 was picked, and lined by the pipette tip on a solid YP culture plate containing Kanamycin (yeast extraction 5 g/L, peptone 10 g/L, sodium chloride 5 g/L, agar 8 g, kanamycin 25 mg/L, pH 7.0), and cultured for 2-3 days at 28° C. in dark. The plaques on the YP culture plate were scraped and cultured on a new YP culture plate for another day; the colonies cultured for 3-4 days were scraped and placed in 30 ml of infestation solution (i.e., infestation medium (MS salt 2.15 g/L, B5 vitamin, sucrose 20 g/L, glucose 10 g/L, AS 40 mg/L, MES 4 g/L, ZT 2 mg/L, pH 5.3)) in a 50 ml centrifuge tube, shaken continuously to completely dilute the bacterial cells in the infestation solution, the diluted Agrobacterium liquid was poured into a 250 ml glass bottle (sterilized) containing 150 ml of infestation solution, and diluted to a certain volume, so that the concentration of the Agrobacterium liquid was adjusted to $OD_{660}$=0.5-0.8, which was stored for later use.

In the infestation medium of the present example, the MS salt might also be N6 salt (concentration was 3.95 g/L) or B5 salt (concentration was 3.1 g/L), and the concentration of sucrose might be 5-100 g/L, the concentration of glucose might be 5-100 g/L, the concentration of AS might be 10-50 mg/L, the concentration of MES might be 0.1-5 g/L, and the concentration of ZT might be 0.1-5 mg/L; the above components could be combined arbitrarily in their concentration ranges, but the infestation medium (MS salt 2.15 g/L, B5 vitamin, sucrose 20 g/L, glucose 10 g/L, AS 40 mg/L, MES 4 g/L, ZT 2 mg/L, pH 5.3) was preferred.

Infestation of soybean meristem block with Agrobacterium: the Agrobacterium liquid (10-15 ml) was placed in contact with the cotyledonary node tissue of the ultrasonically treated soybean meristem block for at least 3 hours, preferably 5 hours; after the end of infestation, the Agrobacterium liquid was sucked out, and the Agrobacterium liquid adhered to the soybean meristem block was thoroughly sopped up with a filter paper.

Co-culture of Agrobacterium and soybean meristem block: The meristem block from which Agrobacterium liquid was sopped up was transferred to a co-culture medium (MS salt 4.3 g/L, B5 vitamin, sucrose 20 g/L, glucose 10 g/L, MES 4 g/L, ZT 2 mg/L, agar 8 g/L, pH 5.6), a filter paper was placed in the medium, and the adaxial surface of cotyledon was facing up, 15 soybean seeds per dish, and co-cultured in a dark incubator at a constant temperature of 22° C. for 2-5 days, preferably for 3 days.

In the above co-culture medium of the present example, the concentration of sucrose might be 5-100 g/L, the concentration of glucose might be 5-100 g/L, and the concentration of MES might be 0.1-5 g/L, the concentration of ZT might be 0.1-5 mg/L; and the above components could combined arbitrarily in their concentration ranges, but the co-culture medium (MS salt 4.3 g/L, B5 vitamin, sucrose 20 g/L, glucose 10 g/L, MES 4 g/L, ZT 2 mg/L, agar 8 g/L, pH 5.6) was preferred.

Restoration of soybean meristem block: the elongated hypocotyl of the meristem block after the co-culture was cut off, and then the meristem block was transferred to a recovery medium after the hypocotyl was cut (B5 salt 3.1 g/L, B5 vitamins, MES 1 g/L, sucrose 30 g/L, ZT 2 mg/L, agar 8 g/L, cephalosporin 150 mg/L, glutamic acid 100 mg/L, aspartic acid 100 mg/L, pH 5.6), recovered for 2-5 days, preferably 3 days, to eliminate Agrobacterium and provide a recovery period for infested cells.

In the above recovery medium of the present example, the concentration of MES might be 0.1-5 g/L, the concentration of sucrose might be 5-100 g/L, the concentration of ZT might be 0.1-5 mg/L, the concentration of cephalosporin might be 100-300 mg/L, the concentration of glutamic acid might be 50-200 mg/L, the concentration of aspartic acid might be 50-200 mg/L; and the above components could be combined arbitrarily in their concentration ranges, but the recovery medium (B5 salt 3.1 g/L, B5 vitamin, MES 1 g/L, sucrose 30 g/L, ZT 2 mg/L, agar 8 g/L, cephalosporin 150 mg/L, glutamic acid 100 mg/L, aspartic acid 100 mg/L, pH 5.6) was preferred.

Screening of soybean meristem block: After the recovery period, the meristem block was transferred to 60 ml of a proliferation medium without a selective agent (tribenuron methyl) (B5 salt 3.1 g/L, B5 vitamin, MES 1 g/L, sucrose 30 g/L, 6-BAP 1 mg/L, agar 8 g/L, cephalosporin 150 mg/L, glutamic acid 100 mg/L, aspartic acid 100 mg/L, pH 5.6), so that the soybean meristem block grew rapidly, and the screening and culturing was carried out for 5-9 days, preferably 7 days, under the conditions of a temperature of 24° C. and a photoperiod (light/dark) of 16:8. After the above soybean meristem block was proliferated for 5-9 days, tribenuron methyl herbicide (95% tribenuron methyl wettable powder) was externally applied in concentration of 1, 3, 5 and 7 µg to per ml of the proliferation medium, respectively, in which the diluted tribenuron methyl herbicide solution was added to the proliferation medium to cause selective growth of the transformed cells, and the screening and culturing was carried out at a temperature of 24° C. and a photoperiod (light/dark) of 16:8 for 2 weeks.

In the proliferation medium of the present embodiment, the B5 salt might also be N6 salt (concentration was 3.95 g/L) or MS salt (concentration was 4.3 g/L), and the concentration of MES might be 0.1-5 g/L, the concentration of sucrose might be 5-100 g/L, the concentration of 6-BAP might be 0.1-5 mg/L, the concentration of cephalosporin might be 100-300 mg/L, the concentration of glutamic acid might be 50-200 mg/L, the concentration of aspartic acid might be 50-200 mg/L; and the above components could can be combined arbitrarily in their concentration ranges, but the proliferation medium (B5 salt 3.1 g/L, B5 vitamins, MES 1 g/L, sucrose 30 g/L, 6-BAP 1 mg/L, agar 8 g/L, cephalosporin 150 mg/L, glutamic acid 100 mg/L, aspartic acid 100 mg/L, pH 5.6) was preferred.

Regeneration of plant from resistant soybean tissue block: The resistant tissue blocks after the above screening treatment with four concentrations of tribenuron methyl were separately taken out from the proliferation medium containing tribenuron methyl, the dead tissues and cotyledons attached thereto were removed, the resistant tissue blocks were transferred to (obliquely inserted into) a B5 differentiation medium without selective agent (tribenuron methyl) (B5 salt 3.1 g/L, B5 vitamin, MES 1 g/L, sucrose 30 g/L, ZT 1 mg/L, agar 8 g/L, cephalosporin 150 mg/L, glutamic acid 50 mg/L, aspartic acid 50 mg/L, gibberellin 1 mg/L, auxin 1 mg/L, pH 5.6), and cultured for differentiation at a temperature of 24° C. and a photoperiod (light/dark) of 16:8 for 14-20 days, preferably 18 days. After the differentiation and growth of the above screened four resistant soybean tissue blocks for 14-20 days, 3, 5 and 7 µg of tribenuron methyl herbicide (95% tribenuron methyl wettable powder) was externally applied to per ml of the B5 differentiation medium, in which the diluted solution of tribenuron methyl herbicide was added dropwise to the B5 differentiation medium by a pipette, and the screening and culturing was continued at a temperature of 24° C. and a photoperiod (light/dark) of 16:8 until the resistant tissue blocks (transformed cells) regenerated into plants or the regenerated plants could survive.

In the above B5 differentiation medium of the present example, the concentration of MES might be 0.1-5 g/L, the concentration of sucrose might be 5-100 g/L, the concentration of ZT might be 0.1-5 mg/L, the concentration of cephalosporin might be 100-300 mg/L, the concentration of glutamic acid might be 50-200 mg/L, the concentration of aspartic acid might be 50-200 mg/L, the concentration of gibberellin might be 0.1-5 mg/L, the concentration of auxin might be 0.1-5 mg/L; and the above components could be combined arbitrarily in their concentration ranges, but the B5 differentiation medium (B5 salt 3.1 g/L, B5 vitamin, MES 1 g/L, sucrose 30 g/L, ZT 1 mg/L, agar 8 g/L, cephalosporin 150 mg/L, glutamic acid 50 mg/L, aspartic acid 50 mg/L, gibberellin 1 mg/L, auxin 1 mg/L, pH 5.6) was preferred.

In the present example, in the screening step of the above soybean meristem blocks and the plant regenerating step of the resistant soybean tissue blocks, the tribenuron methyl herbicide (95% tribenuron methyl wettable powder) was applied to per ml of the proliferation medium or the B5 differentiation medium, and the concentration examples of the diluted tribenuron methyl herbicide solution added dropwise to the proliferation medium or the B5 differentiation medium were shown in Table 1. The proliferated soybean meristem blocks were screened for tolerance to tribenuron methyl herbicide, and the specific information of the 12 treatments was shown in Table 2, and the screening results for each treatment were shown in Table 3, in which each treatment was repeated for 3 times.

TABLE 1

Examples of external application of tribenuron methyl herbicide

| | | | | |
|---|---|---|---|---|
| Dropping concentration of tribenuron methyl herbicide (µg/ml culture medium) | 1 | 3 | 5 | 7 |
| Medium volume (ml/dish) | 60 | 60 | 60 | 60 |
| Concentration of the diluted tribenuron methyl herbicide solution (µg/ml) | 10 | 40 | 50 | 100 |
| Dropping volume of the diluted tribenuron methyl herbicide solution (ml) | 6.0 | 4.5 | 6.0 | 4.2 |
| Dropping mass of tribenuron methyl herbicide (µg/dish) | 60 | 180 | 300 | 420 |

Note: Dropping mass of tribenuron methyl herbicide (µg/dish)=concentration of the diluted tribenuron methyl herbicide solution (µg/ml)×dropping volume of the diluted tribenuron methyl herbicide solution (ml); Dropping concentration of tribenuron methyl herbicide (µg/ml culture medium)=dropping mass of tribenuron methyl herbicide (µg/dish)/medium volume (ml/dish).

TABLE 2

Specific information of 12 different tribenuron methyl screening treatments for soybean meristem blocks

| Treatment | Dropping concentration of tribenuron methyl herbicide (µg/ml proliferation medium) | Dropping concentration of tribenuron methyl herbicide (µg/ml B5 differentiation medium) |
|---|---|---|
| Treatment 1 | 1 | 3 |
| Treatment 2 | 1 | 5 |
| Treatment 3 | 1 | 7 |
| Treatment 4 | 3 | 3 |
| Treatment 5 | 3 | 5 |
| Treatment 6 | 3 | 7 |
| Treatment 7 | 5 | 3 |
| Treatment 8 | 5 | 5 |
| Treatment 9 | 5 | 7 |
| Treatment 10 | 7 | 3 |
| Treatment 11 | 7 | 5 |
| Treatment 12 | 7 | 7 |

The seedlings differentiated from the above 12 treatments were transferred to a B5 rooting medium (B5 salt 3.1 g/L, B5 vitamin, MES 1 g/L, sucrose 30 g/L, agar 8 g/L, cephalosporin 150 mg/L, indole-3-butyric acid (IBA) 1 mg/L, pH 5.6), cultured at 25° C. to a height of about 10 cm, and moved to a greenhouse to grow until fructification. The transgenic plants could be obtained by culturing at 26° C. for 16 hours and then at 20° C. for 8 hours per day in a greenhouse.

In the above B5 rooting medium of the present example, the concentration of MES might be 0.1-5 g/L, the concentration of sucrose might be 5-100 g/L, the concentration of cephalosporin might be 100-300 mg/L, the concentration of IBA might be 0.1-5 mg/L; and the above components could be combined arbitrarily in their concentration ranges, but the B5 rooting medium (B5 salt 3.1 g/L, B5 vitamin, MES 1 g/L, sucrose 30 g/L, agar 8 g/L, cephalosporin 150 mg/L, IBA 1 mg/L, pH 5.6) was preferred.

In the present example, except tribenuron methyl, the preferred embodiments were used for all others.

Example 3. By TaqMan Verification of Soybean Plants which SULE Nucleotide Sequence is Transferred into About 100 mg of the leaves of the soybean plants which SULE nucleotide sequence is transferred into after the above 12 treatments were taken as samples, respectively, the genomic DNA of each sample was extracted with Qiagen's DNeasy Plant Maxi Kit, and the SULE gene copy number thereof was detected by Taqman probe fluorescent quantitative PCR. At the same time, the wild-type soybean plant was used as a control, and the detection and analysis were carried out according to the above method. The experiment was repeated for 3 times and the average value was taken.

The specific method for detecting the copy number of SULE gene was as follows:

Step 11, 100 mg of the leaves of the soybean plants which SULE nucleotide sequence is transferred into after the above 12 treatments and those of the wild-type soybean plant were taken as samples, respectively, and homogenized separately with liquid nitrogen in a mortar, and each sample was repeated for 3 times;

Step 12. the genomic DNA of each of the above samples was extracted by using Qiagen's DNeasy Plant Mini Kit, in which the specific method referred to the product manual thereof;

Step 13. the genomic DNA concentration of each of the above samples was determined by using NanoDrop 2000 (Thermo Scientific);

Step 14, the genomic DNA concentrations of the above samples were adjusted to the same concentration value, in which the concentration value ranged from 80 to 100 ng/μl;

Step 15. the copy numbers of the samples were identified by using Taqman probe fluorescent quantitative PCR method, a sample with a known copy number after identification was used as a standard, the sample of the wild-type soybean plant was used as a control, each sample was repeated for 3 times and the average value was taken; the fluorescent quantitative PCR primer and probe sequences were:

The following primers and probes were used to detect the SULE nucleotide sequence:
Primer 1: TGGGAGAGGAAGGGGTAACAT, as shown in SEQ ID NO: 5 in the Sequence Listing;
Primer 2: TATCTCTCACCCAGGCACCTT, as shown in SEQ ID NO: 6 in the Sequence Listing;
Probe 1: ACGGACCTTTCGGACAGTTGGAGGA, as shown in SEQ ID NO: 7 in the Sequence Listing;
The PCR reaction system was:
JumpStart™ Taq ReadyMix™ (Sigma) 10 μl
50× primer/probe mixture 1 μl
Genomic DNA 3 μl
Water (ddH$_2$O) 6 μl The 50× primer/probe mixture contained 45 μl of each primer at a concentration of 1 mM, 50 μl of probe at a concentration of 100 μM, and 860 μl of 1×TE buffer, and stored at 4° C. in an amber tube.

The PCR reaction conditions were:

| Step | Temperature | Time |
|---|---|---|
| 21 | 95° C. | 5 minutes |
| 22 | 95° C. | 30 seconds |
| 23 | 60° C. | 1 minute |
| 24 | returned to step 22, repeated for 40 times | |

The data were analyzed using SDS2.3 software (Applied Biosystems).

Figure 3:
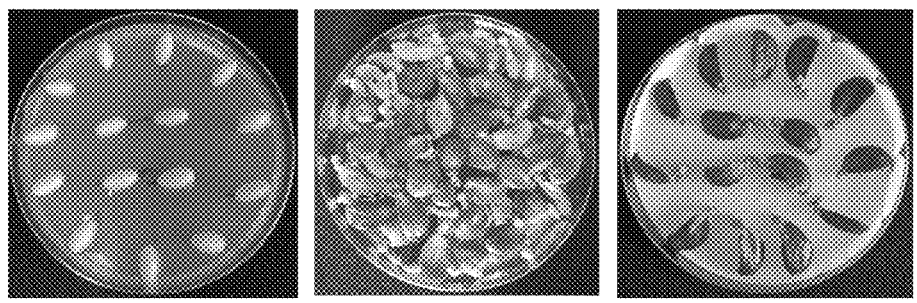
FIG. 3 shows an effect chart of soybean tissue transformation by the method for improving soybean transformation efficiency of the present invention.
Figure 3:
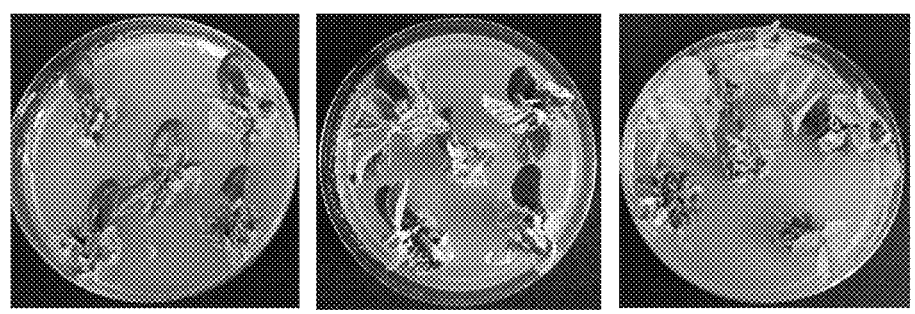
Figure 3:
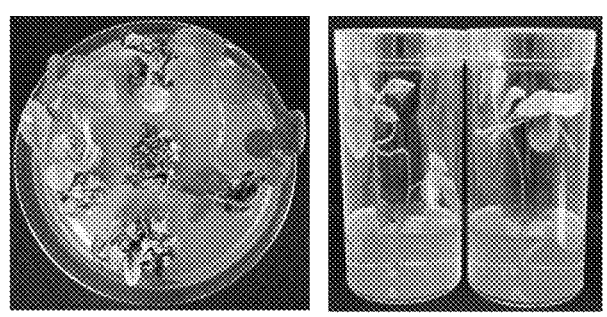

The experimental results showed that the SULE nucleotide sequence was integrated into the genomes of some tested soybean plants (i.e., positive plants), and the experimental results of the 12 treatments were shown in Table 3 and FIG. 3.

TABLE 3

Experimental results of the 12 treatments

| Treatment | Number of initially germinated soybeans (number) | Number of seedlings (plant) | Number of positive plants (plant) | Positive plant rate (%) | Transformation efficiency (%) |
|---|---|---|---|---|---|
| 1 | 50 | 27 | 6 | 22.2 | 12.0 |
| 2 | 55 | 24 | 6 | 25.0 | 10.9 |
| 3 | 75 | 10 | 5 | 50.0 | 6.7 |
| 4 | 55 | 25 | 5 | 20.0 | 9.1 |
| 5 | 60 | 28 | 6 | 21.4 | 10.0 |
| 6 | 45 | 23 | 11 | 47.8 | 24.4 |
| 7 | 50 | 19 | 7 | 36.8 | 14.0 |
| 8 | 70 | 16 | 4 | 25.0 | 5.7 |
| 9 | 43 | 8 | 5 | 62.5 | 11.6 |
| 10 | 80 | 15 | 9 | 60.0 | 11.3 |
| 11 | 75 | 9 | 7 | 77.7 | 9.3 |
| 12 | 80 | 5 | 4 | 80.0 | 5.0 |

Note:
Positive plant rate (%) = number of positive plants (plant)/number of seedlings (plant) × 100%;
Transformation efficiency (%) = number of positive plants (plant)/number of initially germinated soybeans (number) × 100%.

It could be seen in Table 3 that in the screening step of the soybean meristem blocks in the transformation process and the step of regenerating plants from the resistant soybean tissue blocks, the tribenuron methyl herbicide (95% tribenuron methyl wettable powder) was externally applied to per ml of the proliferation medium or the B5 differentiation medium, the screening was carried out by adding dropwise the diluted tribenuron methyl herbicide solution to the proliferation medium or the B5 differentiation medium, and all of the above 12 treatments could achieve relatively higher positive plant rate and transformation efficiency, in which the treatment 6 was better and had a transformation efficiency of 20% or more.

In summary, unlike the prior art, in which the selective agent is disposed in culture medium, the present invention firstly proposes that the selective agent (such as tribenuron methyl) is externally applied (especially added dropwise) to the proliferation medium and the differentiation medium in the plant transformation process, and the positive plant rate and transformation efficiency of the progeny thereof are significantly improved, which provides a new idea for the use of the selective agent in the plant transformation process.

By using the *Agrobacterium*-mediated transformation method, the present invention not only provides a new usage and screening method for using a sulfonylurea herbicide as the selective agent, but also optimizes the effective screening concentration range, thus obtaining a transgenic plant resistant to ALS inhibitor. When a sulfonylurea herbicide is used as the selective agent, the selective agent with an optimized concentration is added in a manner of external application (especially dropping) for screening, and the proportion of positive plants obtained in the progeny thereof is significantly increased, and the transformation efficiency can be as high as 20% or more, and the manner of external application (especially dropping) ensures the effective utilization of the selective agent, thereby reducing the cost of plant genetic transformation. In the meantime, the present invention uses a sulfonylurea herbicide hydrolase gene as a selective marker in the transformation, thereby obtaining transgenic plants with high commercial value, good resistance and improved genetic stability.

It should be noted that the above examples are merely illustrative of the technical solutions of the present invention, and are not intended to be limiting. Although the present invention is described in detail with reference to the preferred examples, those skilled in the art will understand that modifications or equivalents may be made without departing from the spirit and scope of the invention.

What is claimed is:

1. A method for producing a transformed soybean plant, which comprises:
   (a) excising the meristem from a soybean plant to produce a meristem block;
   (b) introducing a recombinant vector containing a gene of interest and a gene encoding a sulfonylurea herbicide hydrolase to the meristem block, wherein the sulfonylurea herbicide hydrolase comprises: (a) a protein composed of an amino acid sequence as shown in SEQ ID NO: 2; or (b) a protein derived from the protein in (a) by substitution and/or deletion and/or addition of one or several amino acids in the amino acid sequence as shown in SEQ ID NO: 2 and having an aryloxyalkanoate dioxygenase activity; or (c) a protein composed of an amino acid sequence having at least 90% sequence identity to SEQ ID NO: 2;
(c) placing the meristem block on a medium;
(d) spraying a tribenuron methyl on the meristem block on the proliferation medium to select for transformed resistant tissue and 1-7 μg of tribenuron methyl is externally applied to per ml of the proliferation medium, and
(e) regenerating the transformed resistant tissue into a soybean plant, wherein the regeneration is done by placing the transformed resistant tissue on a medium and spraying a tribenuron methyl on the transformed resistant tissue,
wherein the transformation rate of the method is higher than the transformation rate obtained from a method in which the tribenuron methyl is added to the medium prior to placing the meristem block on the medium.

2. The method for producing a transformed soybean plant according to claim 1, wherein 3 μg of tribenuron methyl is externally applied to per ml of the proliferation medium.

3. A method of transforming a soybean, which comprises:
removing one cotyledon and the first true leaf after the germination of a soybean seed, to obtain a naked meristem block with one cotyledon;
performing pretreatment by inoculating the naked meristem block with one cotyledon onto a pretreatment medium containing a cytokinin;
introducing a recombinant vector containing a gene of interest and a gene encoding a sulfonylurea herbicide hydrolase to the meristem block, wherein the sulfonylurea herbicide hydrolase comprises: (a) a protein composed of an amino acid sequence as shown in SEO ID NO: 2; or (b) a protein derived from the protein in (a) by substitution and/or deletion and/or addition of one or several amino acids in the amino acid sequence as shown in SEO ID NO: 2 and having an aryloxyalkanoate dioxygenase activity; or (c) a protein composed of an amino acid sequence having at least 90% sequence identity to SEO ID NO: 2;
placing the meristem block on a medium; spraying a tribenuron methyl on the meristem block on the proliferation medium to select for transformed resistant tissue and 1-7 ug of tribenuron methyl is externally applied to per ml of the proliferation medium; and
selecting a soybean plant cell that has not been killed and/or not been inhibited,
wherein the transformation rate of the method is higher than the transformation rate obtained from a method in which the tribenuron methyl is added to the medium prior to placing the meristem block on the medium.

4. The method of transforming a soybean according to claim 3, wherein the cytokinin is any one or any combination of 1 mg/L 6-benzylaminopurine and 2 mg/L zeatin.

5. The method of transforming a soybean according to claim 3, wherein 3 μg of tribenuron methyl is applied to per ml of the proliferation medium.

6. A method of producing a stably transformed soybean plant, which comprises:
removing one cotyledon and the first true leaf after the germination of a soybean seed, to obtain a naked meristem block with one cotyledon;
performing pretreatment by inoculating the naked meristem block with one cotyledon onto a pretreatment medium containing a cytokinin;
introducing a recombinant vector containing a gene of interest and a gene encoding a sulfonylurea herbicide hydrolase to the meristem block, wherein the sulfonylurea herbicide hydrolase comprises: (a) a protein composed of an amino acid sequence as shown in SEQ ID NO: 2; or (b) a protein derived from the protein in (a) by substitution and/or deletion and/or addition of one or several amino acids in the amino acid sequence as shown in SEQ ID NO: 2 and having an aryloxyalkanoate dioxygenase activity; or (c) a protein composed of an amino acid sequence having at least 90% sequence identity to SEQ ID NO: 2;
placing the meristem block on a medium;
spraying a tribenuron methyl on the meristem block on the proliferation medium to select for transformed resistant tissue and 1-7 μg of tribenuron methyl is externally applied to per ml of the proliferation medium;
regenerating the transformed resistant tissue into a soybean plant, wherein the regeneration is done by placing the transformed resistant tissue on a medium and spraying a tribenuron methyl on the transformed resistant tissue,
wherein the transformation rate of the method is higher than the transformation rate obtained from a method in which the tribenuron methyl is added to the medium prior to placing the meristem block on the medium.

7. The method of producing a stably transformed soybean plant according to claim 6, wherein 3-7 ug of tribenuron methyl is applied to per ml of the differentiation medium.

8. The method of producing a stably transformed soybean plant according to claim 7, wherein 7 μg of tribenuron methyl is applied to per ml of the differentiation medium.

9. The method for producing a transformed soybean plant according to claim 1, wherein the medium of (c) is free of the tribenuron methyl.

* * * * *

SEQUENCE LISTING

```
<160> NUMBER OF SEQ ID NOS: 7

<210> SEQ ID NO 1
<211> LENGTH: 1110
<212> TYPE: DNA
<213> ORGANISM: Artificial sequence
<220> FEATURE:
<223> OTHER INFORMATION: Nucleotide sequence of sulfonylurea herbicide
      hydrolase gene

<400> SEQUENCE: 1
atggagactg ataacgtgga actcgcccaa tctaagagaa aggtggtgct ggctgaacaa      60
gggtcatttt acataggggg taggactgtt actggtcctg gcaagtttga tccatccaaa     120
cctgtgatac cctacagtaa cgaaggagca acattctata ttaaccaaat gtatgttaac     180
ttccaggccc cagtgagacc taggggactt ccattggttt tctggcatgg aggtggcttg     240
actggtcaca tctgggagtc tacacctgac ggcagacccg ggtttcaaac cctcttcgtt     300
caggataggc ataccgtgta cactattgac caacctggga gaggaagggg taacatccca     360
acttttaacg gacctttcgg acagtggag gaagagagta ttgttaacac tgtgacagga     420
aattcttcaa aggaaggtgc ctgggtgaga gataggcttg gccctgctcc cgggcaattt     480
ttcgagaact ctcagtttcc tagaggctat gaagacaatt actttaagga gatgggattc     540
agcccatcta tatccagtga tgaaattgtt gacgctgttg tgaaactcgt gacccatatt     600
ggtccttgtg ttctggtgac tcactcagca tccggcgttc ttgggatgag agtggctaca     660
cacgcaaaga atgttagggg aattgtggcc tatgaaccag ctacctcaat cttccccaag     720
ggaaaagttc cagagatacc acctctcgct gataagaaaa gccaaatctt tcccccattc     780
gaaatacagg agtcttactt taagaaactt gccaagattc caatccaatt tgttttcgga     840
gataacatcc ccaagaatcc aaaatcagca tattggttcc tggactggtg gagagtgaca     900
agatacgcac atagtctcag cctggaggcc ataaacaaat tgggggggaca agcttccctt     960 ttggatcttc ctactgcagg attgagaggt aatacacact ttcccttcac cgataggaac    1020
aatgttcagg tggcttctct cctgtcagac tttctgggta aacacggtct ggatcaaaat    1080
gagagcaaac tcgccgccgc cctggaatga                                     1110

<210> SEQ ID NO 2
<211> LENGTH: 369
<212> TYPE: PRT
<213> ORGANISM: Artificial sequence
<220> FEATURE:
<223> OTHER INFORMATION: Amino acid sequence of sulfonylurea herbicide
      hydrolase gene

<400> SEQUENCE: 2
```

```
Met Glu Thr Asp Asn Val Glu Leu Ala Gln Ser Lys Arg Lys Val Val
1               5                   10                  15

Leu Ala Glu Gln Gly Ser Phe Tyr Ile Gly Gly Arg Thr Val Thr Gly
            20                  25                  30

Pro Gly Lys Phe Asp Pro Ser Lys Pro Val Ile Pro Tyr Ser Asn Glu
            35                  40                  45

Gly Ala Thr Phe Tyr Ile Asn Gln Met Tyr Val Asn Phe Gln Ala Pro
50                  55                  60

Val Arg Pro Arg Gly Leu Pro Leu Val Phe Trp His Gly Gly Gly Leu
65                  70                  75                  80

Thr Gly His Ile Trp Glu Ser Thr Pro Asp Gly Arg Pro Gly Phe Gln
                85                  90                  95

Thr Leu Phe Val Gln Asp Arg His Thr Val Tyr Thr Ile Asp Gln Pro
            100                 105                 110

Gly Arg Gly Arg Gly Asn Ile Pro Thr Phe Asn Gly Pro Phe Gly Gln
            115                 120                 125

Leu Glu Glu Ser Ile Val Asn Thr Val Thr Gly Asn Ser Ser Lys
            130                 135                 140

Glu Gly Ala Trp Val Arg Asp Arg Leu Gly Pro Ala Pro Gly Gln Phe
145                 150                 155                 160

Phe Glu Asn Ser Gln Phe Pro Arg Gly Tyr Glu Asp Asn Tyr Phe Lys
                165                 170                 175

Glu Met Gly Phe Ser Pro Ser Ile Ser Ser Asp Glu Ile Val Asp Ala
            180                 185                 190

Val Val Lys Leu Val Thr His Ile Gly Pro Cys Val Leu Val Thr His
            195                 200                 205

Ser Ala Ser Gly Val Leu Gly Met Arg Val Ala Thr His Ala Lys Asn
210                 215                 220

Val Arg Gly Ile Val Ala Tyr Glu Pro Ala Thr Ser Ile Phe Pro Lys
225                 230                 235                 240

Gly Lys Val Pro Glu Ile Pro Pro Leu Ala Asp Lys Lys Ser Gln Ile
            245                 250                 255

Phe Pro Pro Phe Glu Ile Gln Glu Ser Tyr Phe Lys Lys Leu Ala Lys
            260                 265                 270

Ile Pro Ile Gln Phe Val Phe Gly Asp Asn Ile Pro Lys Asn Pro Lys
            275                 280                 285

Ser Ala Tyr Trp Phe Leu Asp Trp Trp Arg Val Thr Arg Tyr Ala His
290                 295                 300

Ser Leu Ser Leu Glu Ala Ile Asn Lys Leu Gly Gly Gln Ala Ser Leu
305                 310                 315                 320

Leu Asp Leu Pro Thr Ala Gly Leu Arg Gly Asn Thr His Phe Pro Phe
            325                 330                 335

Thr Asp Arg Asn Asn Val Gln Val Ala Ser Leu Leu Ser Asp Phe Leu
            340                 345                 350

Gly Lys His Gly Leu Asp Gln Asn Glu Ser Lys Leu Ala Ala Ala Leu
            355                 360                 365

Glu
```

<210> SEQ ID NO 3
<211> LENGTH: 530
<212> TYPE: DNA
<213> ORGANISM: Cauliflower mosaic virus

<400> SEQUENCE: 3

```
ccatggagtc aaagattcaa atagaggacc taacagaact cgccgtaaag actggcgaac    60
agttcataca gagtctctta cgactcaatg acaagaagaa aatcttcgtc aacatggtgg   120
agcacgacac gcttgtctac tccaaaaata tcaaagatac agtctcagaa gaccaaaggg   180
caattgagac ttttcaacaa agggtaatat ccggaaacct cctcggattc cattgcccag   240
ctatctgtca ctttattgtg aagatagtgg aaaaggaagg tggctcctac aaatgccatc   300
attgcgataa aggaaaggcc atcgttgaag atgcctctgc cgacagtggt cccaaagatg   360
gacccccacc cacgaggagc atcgtggaaa agaagacgt tccaaccacg tcttcaaagc    420
aagtggattg atgtgatatc tccactgacg taagggatga cgcacaatcc cactatcctt   480
cgcaagaccc ttcctctata taaggaagtt catttcattt ggagaggaca             530

<210> SEQ ID NO 4
<211> LENGTH: 195
<212> TYPE: DNA
<213> ORGANISM: Cauliflower mosaic virus

<400> SEQUENCE: 4
ctgaaatcac cagtctctct ctacaaatct atctctctct ataataatgt gtgagtagtt    60
cccagataag ggaattaggg ttcttatagg gtttcgctca tgtgttgagc atataagaaa   120
cccttagtat gtatttgtat ttgtaaaata cttctatcaa taaatttct aattcctaaa    180 accaaaatcc agtgg                                                    195

<210> SEQ ID NO 5
<211> LENGTH: 21
<212> TYPE: DNA
<213> ORGANISM: Artificial sequence
<220> FEATURE:
<223> OTHER INFORMATION: Primer 1

<400> SEQUENCE: 5
tgggagagga aggggtaaca t                                              21

<210> SEQ ID NO 6
<211> LENGTH: 21
<212> TYPE: DNA
<213> ORGANISM: Artificial sequence
<220> FEATURE:
<223> OTHER INFORMATION: Primer 2

<400> SEQUENCE: 6
tatctctcac ccaggcacct t                                              21

<210> SEQ ID NO 7
<211> LENGTH: 25
<212> TYPE: DNA
<213> ORGANISM: Artificial sequence
<220> FEATURE:
<223> OTHER INFORMATION: Probe 1

<400> SEQUENCE: 7
acggaccttt cggacagttg gagga                                          25
```